(12) United States Patent
Lindfors

(10) Patent No.: US 7,473,693 B2
(45) Date of Patent: Jan. 6, 2009

(54) STABLE DISPERSION OF SOLID PARTICLES COMPRISING A WATER-INSOLUBLE PYRAZINE COMPOUND

(75) Inventor: Lennart Lindfors, Mölndal (SE)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 10/543,264

(22) PCT Filed: Feb. 2, 2004

(86) PCT No.: PCT/GB2004/000416

§ 371 (c)(1),
(2), (4) Date: Jul. 25, 2005

(87) PCT Pub. No.: WO2004/069277

PCT Pub. Date: Aug. 19, 2004

(65) Prior Publication Data

US 2006/0134146 A1    Jun. 22, 2006

(30) Foreign Application Priority Data

Feb. 6, 2003    (GB) .................... 0302673.9

(51) Int. Cl.
*A61K 31/495* (2006.01)
*C07D 253/06* (2006.01)
*C07D 401/00* (2006.01)

(52) U.S. Cl. ................................. 514/255.06

(58) Field of Classification Search ............... 424/464, 424/489, 434; 514/2, 252.1, 255
See application file for complete search history.

(56) References Cited

U.S. PATENT DOCUMENTS

| | | | |
|---|---|---|---|
| 4,348,385 A | 9/1982 | Synek |
| 4,610,868 A | 9/1986 | Fountain et al. |
| 4,826,689 A | 5/1989 | Violanto et al. |
| 4,997,454 A | 3/1991 | Violanto et al. |
| 5,100,591 A | 3/1992 | Cerfontaine et al. |
| 5,118,528 A | 6/1992 | Fessi et al. |
| 5,145,648 A | 9/1992 | Miyahara et al. |
| 5,145,684 A | 9/1992 | Liversidge et al. |
| 5,314,506 A | 5/1994 | Midler, Jr. et al. |
| 5,468,604 A | 11/1995 | Zengerle et al. |
| 5,624,941 A | 4/1997 | Barth et al. |
| 5,665,331 A | 9/1997 | Bagchi et al. |
| 5,780,062 A | 7/1998 | Frank et al. |
| 5,843,465 A | 12/1998 | Lundquist |
| 5,858,410 A | 1/1999 | Muller et al. |
| 5,932,245 A | 8/1999 | Wunderlich et al. |
| 6,048,550 A | 4/2000 | Chan et al. |
| 6,074,986 A | 6/2000 | Mulqueen et al. |
| 6,127,520 A * | 10/2000 | Ueda et al. .................... 530/350 |
| 6,375,986 B1 * | 4/2002 | Ryde et al. .................... 424/489 |
| 6,383,471 B1 | 5/2002 | Chen et al. |
| 6,432,984 B1 | 8/2002 | Barth et al. |
| 6,645,985 B2 | 11/2003 | Barth et al. |
| 6,884,438 B1 | 4/2005 | Quintanar et al. |
| 2002/0188007 A1 | 12/2002 | Barth et al. |
| 2003/0059472 A1 | 3/2003 | Brynjelsen et al. |
| 2004/0039024 A1 | 2/2004 | Barth et al. |
| 2005/0009908 A1 | 1/2005 | Hedberg et al. |
| 2005/0202092 A1 | 9/2005 | Skantze et al. |
| 2006/0141043 A1 | 6/2006 | Lindfors |
| 2006/0198893 A1 | 9/2006 | Lindfors |

FOREIGN PATENT DOCUMENTS

| | | |
|---|---|---|
| EP | 275607 | 7/1988 |
| EP | 0377457 | 7/1990 |
| EP | 589838 | 3/1994 |
| GB | 2276567 | 5/1994 |
| JP | 03188438 | 8/1991 |
| WO | WO 92/02513 * | 2/1992 |
| WO | WO-92/02513 A | 2/1992 |
| WO | 9218105 | 10/1992 |
| WO | 9624340 | 8/1996 |
| WO | 9632095 | 10/1996 |

(Continued)

OTHER PUBLICATIONS

E.C. Taylor, Jr., John A. Carbon and Dale R. Hoff, Pteridines. X. New Approach to the Synthesis of Pteridines, Journal of American Chemical Society, vol. 75, 1904-1908, 1953.*

(Continued)

*Primary Examiner*—Michael G. Hartley
*Assistant Examiner*—Jagadishwar Samala
(74) *Attorney, Agent, or Firm*—Pepper Hamilton LLP

(57) ABSTRACT

A process for the preparation of a stable dispersion of solid particles, in an aqueous medium comprising combining (a) a first solution comprising a substantially water-insoluble substance which is a pyrazine compound of Formula I, a water-miscible organic solvent and an inhibitor with (b) an aqueous phase comprising water and optionally a stabilizer, thereby precipitating solid particles comprising the inhibitor and the substantially water-insoluble substance; and optionally removing the water-miscible organic solvent; wherein the inhibitor is a non-polymeric hydrophobic organic compound as defined in the description.

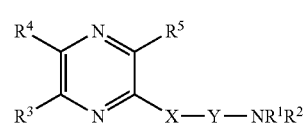

I

Also claimed are stable dispersions prepared by the process, solid particles prepared by the process and use of such particles.

11 Claims, No Drawings

FOREIGN PATENT DOCUMENTS

| WO | 9635414 | 11/1996 |
|---|---|---|
| WO | 9704756 | 2/1997 |
| WO | 9711686 | 4/1997 |
| WO | 9713503 | 4/1997 |
| WO | 9807414 | 2/1998 |
| WO | 9814174 | 4/1998 |
| WO | 9823350 | 6/1998 |
| WO | 9900113 | 1/1999 |
| WO | 9904766 | 2/1999 |
| WO | 9959709 | 11/1999 |
| WO | 0033820 | 6/2000 |
| WO | 0038811 | 7/2000 |
| WO | 0044468 | 8/2000 |
| WO | 0071079 | 11/2000 |
| WO | 0170700 | 9/2001 |
| WO | 0192293 | 12/2001 |
| WO | 0200199 | 1/2002 |
| WO | 02055059 | 7/2002 |
| WO | WO-03/013472 A | 2/2003 |
| WO | 03035035 | 5/2003 |
| WO | 0351850 | 6/2003 |
| WO | 0351851 | 6/2003 |
| WO | WO-03/051851 A | 6/2003 |

OTHER PUBLICATIONS

E.C. Taylor, Jr., John A. Carbon and Dale R. Hoff, Pteridines. X New Approach to the Synthesis of Pteridines, journal of American Chemical Socieity, vol. 75, 1904-1908, 1953.*

W.R. Boon and G. Bratt, Pteridines. Part V. Derivatives of 1:4-Dihydro-1-and 3:4-Dihydro-3-methyl-6 : 7-diphenylpteridine, J. of Chemical Society, 2159-2161, 1957.*

International Search Report from PCT/GB2004/000416 Jan. 7, 2004.

Final Rejection dated Mar. 26, 2008 cited in Copending Application No. 10/486,211.

Non-final Office Action dated Jul. 26, 2007 cited in Copending Application No. 10/486,211.

Welin-Berger et al., "Inhibition of Ostwald ripening in local anesthetic emulsions by using hydrophobic excipients in the disperse phase," Int J Pharmeceut, (2000) 200(2):249-260.

Ostwald, "[Uber die vermeintliche Isomeric des roten und gelben Quecksilberoxyds und die Oberflachenspannung gester Korper,]" Phys. Chem. (1900) 34:495-503.

Higuchi et al., "Physical degradation of emulsions via the molecular diffusion route and the possible prevention thereof," J Pharm Sci (1962) 51:459-466.

Kabalnov et al., "Ostwald ripening in two-component disperse phase systems: application to emulsion stability," Colloids and Surface (1987) 24:19-32.

Lannibois et al., "Surfactant limited aggregation of hydrophobic molecules in water," Journal Phys II France (1997) 7:319-342.

Lowe "Second-generation perfluorocarbon emulsion blood substitutes," Artificial Cell Blood Substitutes and Immob Biotech (2000) 28(1):25-38.

Harding "The influence of Iodide content on the ripening behavior of a model emulsion system," Photographic Science Engineering (1980) 24(1):32-44.

Steffens et al., "O/W Emulsions as Vehicles for Micronized Drug Particles," Eur J Pharm, Biopharm (1991) 37 (4):219-226.

Ruch et al., "Preparation of Micrometer Size Budesonide Particles by Precipitation," Journal of Colloid and Interface Science (2000) 229(1):207-211.

Malcolmson et al., "Effect of oil on the level of solubilization of testosterone propionate into nonionic oil-in-water microemulsions," J Pharm Sci (1998) 87(1):109-116.

Sjostrom et al., "The formation of submicron organic particles by precipitation in an emulsion," J Dispersion Science and Tech (1994) 15(1):89-117.

Sjostrom et al., "A method for the preparation of submicron particles of sparingly water-soluble drugs by precipitation in oil-in-water emulsions. II: influence of the emulsifier, the solvent, and the drug substance," J Pharm Sci (1993) 82 (6):584-589.

Kasai et al., "Crystal growth of perylene microcrystals in the reprecipitation method," Bull Chem Soc Jpn (1998) 71:2597-2601.

Kasai et al., "A novel preparation method of organic microcrystals," Jpn J Appl Phys (1992) 31:L1132-1134.

Mohwald et al., "Imaging and other techniques," Current Opinion in Colliod and Interface Science (1997) 2:129-130.

Goddard, "Polymer-Surfactant interaction Part I. Uncharged water-soluble polymers and charged surfactants," Colloids and Surfaces (1986) 19:255-300.

Scalzo et al., Farmaco, Societa Chimica Italiana (1988) 43(9):677-691.

* cited by examiner

STABLE DISPERSION OF SOLID PARTICLES COMPRISING A WATER-INSOLUBLE PYRAZINE COMPOUND

RELATED APPLICATIONS

This application is a national stage filing under 35 U.S.C. 371 of International Application PCT/GB2004/000416, filed Feb. 2, 2004, which claims priority from United Kingdom Patent Application No. 0302673.9, filed Feb. 6, 2003, the specifications of each of which are incorporated by reference herein. International Application PCT/GB2004/000416 was published under PCT Article 21(2) in English.

The present invention relates to a process for the preparation of a stable dispersion of particles, particularly sub-micron particles in an aqueous medium and to a stable dispersion of particles in a liquid medium, more particularly to a process for the preparation of a dispersion of particles comprising a substantially water-insoluble pharmacologically active pyrazine carboxamide compound of formula I in an aqueous medium, which particles exhibit substantially no increase in size upon storage in the aqueous medium, in particular to aqueous dispersions of particles that exhibit substantially no particle growth mediated by Ostwald ripening.

Dispersions of a solid material in a liquid medium are required for a number of different applications including paints, inks, dispersions of pesticides and other agrochemicals, dispersions of biocides and dispersions of pharmacologically active compounds. In the pharmaceutical field many pharmacologically active compounds have very low aqueous solubility which can result in low bioavailability when such compounds are administered to a patient. The bioavailability of such compounds may be improved by reducing the particle size of the compound, particularly to a sub-micron size, because this improves dissolution rate and hence absorption of the compound.

The formulation of a pharmacologically active compound as an aqueous suspension, particularly a suspension with a sub-micron particle size, enables the compound to be administered intravenously thereby providing an alternative route of administration which may increase bioavailability compared to oral administration.

Generally however, if there is a range of particles sizes dispersed in a medium there will be a differential rate of dissolution of the particles in the medium. The differential dissolution results in the smaller particles being thermodynamically unstable relative to the larger particles and gives rise to a flux of material from the smaller particles to the larger particles. The effect of this is that the smaller particles dissolve in the medium, whilst material is deposited onto the larger particles thereby giving an increase in particle size. One such mechanism for particle growth is known as Ostwald ripening (Ostwald, Z Phys. Chem. (34), 1900, 495-503).

The growth of particles in a dispersion can result in instability of the dispersion during storage resulting in the sedimentation of particles from the dispersion. It is particularly important that the particle size in a dispersion of a pharmacologically active compound remains constant because a change in particle size is likely to affect the bioavailability and hence the efficacy of the compound. Furthermore, if the dispersion is required for intravenous administration, growth of the particles in the dispersion may render the dispersion unsuitable for this purpose, possibly leading to adverse or dangerous side effects.

Theoretically particle growth resulting from Ostwald ripening would be eliminated if all the particles in the dispersion were the same size. However, in practice, it is not possible to achieve a completely uniform particle size and even small differences in particle sizes can give rise to particle growth.

Aqueous suspensions of a solid material can be prepared by mechanical fragmentation, for example by milling. U.S. Pat. No. 5,145,648 describes wet milling of a suspension of a sparingly soluble compound in an aqueous medium. However, mechanical fragmentation of a material, for example by milling, generally gives a wide distribution of particle sizes. Furthermore, mechanical fragmentation is less efficient in terms of particle size reduction when applied to non-crystalline starting material.

U.S. Pat. No. 4,826,689 describes a processes for the preparation of uniform sized particles of a solid by infusing an aqueous precipitating liquid into a solution of the solid in an organic liquid under controlled conditions of temperature and infusion rate, thereby controlling the particle size. U.S. Pat. No. 4,997,454 describes a similar process in which the precipitating liquid is non-aqueous. However, when the particles have a small but finite solubility in the precipitating medium particle size growth is observed after the particles have been precipitated. To maintain a particular particle size using these processes it is necessary to isolate the particles as soon as they have been precipitated to minimise particle growth. Therefore, particles prepared according to these processes cannot be stored in a liquid medium as a dispersion. Furthermore, for some materials the rate of Ostwald ripening is so great that it is not practical to isolate small particles (especially nanoparticles) from the suspension.

W. J. Higuchi and J. Misra (J. Pharm. Sci., 51 (1962) 459) describe a method for inhibiting the growth of the oil droplets in oil-in-water emulsions by adding a hydrophobic compound (such as hexadecane) to the oil phase of the emulsion. U.S. Pat. No. 6,074,986 (WO95/07614) describes the addition of a polymeric material having a molecular weight of up to 10,000 to the disperse oil phase of an oil-in-water emulsion to inhibit Ostwald ripening. Welin-Berger et al. (Int. Jour. of Pharmaceutics 200 (2000) pp 249-260) describe the addition of a hydrophobic material to the oil phase of an oil-in-water emulsion to inhibit Ostwald ripening of the oil droplets in the emulsion. In these latter three references the material added to the oil phase is dissolved in the oil phase to give a single phase oil dispersed in the aqueous continuous medium.

EP 589 838 describes the addition of a polymeric stabilizer to stabilize an oil-in-water emulsion wherein the disperse phase is a hydrophobic pesticide dissolved in a hydrophobic solvent.

U.S. Pat. No. 4,348,385 discloses a dispersion of a solid pesticide in an organic solvent to which is added an ionic dispersant to control Ostwald ripening.

WO 99/04766 describes a process for preparing vesicular nano-capsules by forming an oil-in-water emulsion wherein the dispersed oil phase comprises a material designed to form a nano-capsule envelope, an organic solvent and optionally an active ingredient. After formation of a stable emulsion the solvent is extracted to leave a dispersion of nano-capsules.

U.S. Pat. No. 5,100,591 describes a process in which particles comprising a complex between a water insoluble substance and a phospholipid are prepared by co-precipitation of the substance and phospholipid into an aqueous medium. Generally the molar ratio of phospholipid to substance is 1:1 to ensure that a complex is formed.

U.S. Pat. No. 4,610,868 describes lipid matrix carriers in which particles of a substance is dispersed in a lipid matrix. The major phase of the lipid matrix carrier comprises a hydrophobic lipid material such as a phospholipid.

Patent Cooperation Treaty Application no PCT/GB02/05472 discloses pyrazine carboxamides of Formula I

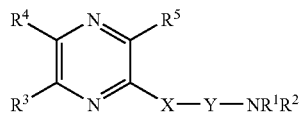

and pharmaceutically acceptable salts, prodrugs, solvates and crystalline forms thereof, in which $R^1$ and $R^2$ independently represent:

a $C_{1-6}$alkyl group;

an (amino)$C_{1-4}$alkyl-group in which the amino is optionally substituted by one or more $C_{1-3}$alkyl groups;

an optionally substituted non-aromatic $C_{3-15}$carbocyclic group;

a ($C_{3-12}$cycloalkyl)$C_{1-3}$alkyl-group;

a group —$CH_2)_r$(phenyl)$_s$ in which r is 0, 1, 2, 3 or 4, s is 1 when r is 0 otherwise s is 1 or 2 and the phenyl groups are optionally independently substituted by one, two or three groups represented by Z;

naphthyl;

anthracenyl;

a saturated 5 to 8 membered heterocyclic group containing one nitrogen and optionally one of the following: oxygen, sulphur or an additional nitrogen wherein the heterocyclic group is optionally substituted by one or more $C_{1-3}$alkyl groups, hydroxy or benzyl; 1-adamantylmethyl;

a group —$(CH_2)_t$ Het in which t is 0, 1, 2, 3 or 4, and the alkylene chain is optionally substituted by one or more $C_{1-3}$alkyl groups and Het represents an aromatic heterocycle optionally substituted by one, two or three groups selected from a $C_{1-5}$alkyl group, a $C_{1-5}$alkoxy group or halo;

or $R^1$ represents H and $R^2$ is as defined above;

or $R^1$ and $R^2$ together with the nitrogen atom to which they are attached represent a saturated 5 to 8 membered heterocyclic group containing one nitrogen and optionally one of the following: oxygen, sulphur or an additional nitrogen; wherein the heterocyclic group is optionally substituted by one or more $C_{1-3}$alkyl groups, hydroxy or benzyl;

X is CO or $SO_2$;

Y is absent or represents NH optionally substitututed by a $C_{1-3}$alkyl group;

$R^3$ and $R^4$ independently represent phenyl, thienyl or pyridyl each of which is optionally substituted by one, two or three groups represented by Z;

Z represents a $C_{1-3}$alkyl group, a $C_{1-3}$alkoxy group, hydroxy, halo, trifluoromethyl, trifluoromethylthio, trifluoromethoxy, trifluoromethylsulphonyl, nitro, amino, mono or di $C_{1-3}$alkylamino, mono or di $C_{1-3}$alkylamido, $C_{1-3}$alkylsulphonyl, $C_{1-3}$alkoxycarbonyl, carboxy, cyano, carbamoyl, mono or di $C_{1-3}$alkyl carbamoyl, sulphamoyl and acetyl; and $R^5$ is H, a $C_{1-3}$alkyl group, a $C_{1-3}$alkoxymethyl group, trifluoromethyl, a hydroxy$C_{1-3}$alkyl group, $C_{1-3}$alkoxycarbonyl, carboxy, cyano, carbamoyl, mono or di $C_{1-3}$alkylcarbamoyl, acetyl, or hydrazinocarbonyl of formula —$CONHNR^aR^b$ wherein $R^a$ and $R^b$ are as previously defined for $R^1$ and $R^2$ respectively;

and their use in the treatment of obesity, psychiatric and neurological disorders. Such compounds are herineafter referred to as a compound of Formula I.

We have surprisingly found that stable dispersions of solid particles of a compound of Formula I in an aqueous medium can be prepared using a precipitation process without the need for water-immiscible solvents or the formation of an emulsion. The dispersions prepared according to the present invention exhibit little or no particle growth after precipitation mediated by Ostwald ripening.

According to a first aspect of the present invention there is provided a process for the preparation of a stable dispersion of solid particles in an aqueous medium comprising:

combining (a) a first solution comprising a substantially water-insoluble substance which is a compound of Formula I, a water-miscible organic solvent and an inhibitor with (b) an aqueous phase comprising water and optionally a stabiliser, thereby precipitating solid particles comprising the inhibitor and the substantially water-insoluble substance; and optionally removing the water-miscible organic solvent; wherein:

(i) the inhibitor is a non-polymeric hydrophobic organic compound that is substantially insoluble in water;

(ii) the inhibitor is less soluble in water than the substantially water-insoluble substance; and (iii) the inhibitor is not a phospholipid.

The process according to the present invention enables stable dispersions of very small articles, especially nanoparticles, to be prepared in high concentration without the need to quickly isolate the particles from the liquid medium into which they have been precipitated to prevent particle growth.

The dispersion according to the present invention is stable, by which we mean that the solid particles in the dispersion exhibit reduced or substantially no particle growth mediated by Ostwald ripening. By the term "reduced particle growth" is meant that the rate of particle growth mediated by Ostwald ripening is reduced compared to particles prepared without the use of an inhibitor. By the term "substantialy no particle growth" is meant that the mean particle size of the particles in the aqueous medium does not increase by more than 10% (more preferably by not more than 5%) over a period of 1 hour at 20° C. after precipitation into the aqueous phase in the present process. Preferably the particles exhibit substantially no particle growth.

It is to be understood that in those cases where the solid particles are precipitated in an amorphous form the resulting particles will, generally, eventually revert to a thermodynamically more stable crystalline form upon storage as an aqueous dispersion. The time taken for such dispersions to re-crystallise is dependent upon the substance and may vary from a few hours to a number of days. Generally such re-crystallisation will result in particle growth and the formation of large crystalline particles which are prone to sedimentation from the dispersion. It is to be understood that the present invention does not prevent conversion of amorphous particles in the suspension into a crystalline state. The presence of the inhibitor in the particles according to the present invention significantly reduces or eliminates particle growth mediated by Ostwald ripening, as hereinbefore described. The particles are therefore stable to Ostwald ripening and the term "stable" used herein is to be construed accordingly.

The solid particles in the dispersion preferably have a mean particle size of less than 10 μm, more preferably less than 5 μm, still more preferably less than 1 μm and especially less than 500 nm. It is especially preferred that the particles in the dispersion have a mean particle size of from 10 to 500 nm, more especially from 50 to 300 nm and still more especially from 100 to 200 nm. The mean size of the particles in the dispersion may be measured using conventional techniques, for example by dynamic light scattering to measure the intensity-averaged particle size.

Generally the solid particles in the dispersion prepared according to the present invention exhibit a narrow unimodal particle size distribution.

The solid particles may be crystalline, semi-crystalline or amorphous. In an embodiment, the solid particles comprise a compound of Formula I in a substantially amorphous form. This can be advantageous as many pharmacological compounds exhibit increased bioavailability in amorphous form compared to their crystalline or semi-crystalline forms. The precise form of the particles obtained will depend upon the conditions used during the precipitation step of the process. Generally, the present process results in rapid precipitation of the substance and the formation of substantially amorphous particles.

By substantially insoluble is meant a substance that has a solubility in water at 25° C. of less than 0.5 mg/ml, preferably less than 0.1 mg/ml and especially less than 0.05 mg/ml.

The greatest effect on particle growth inhibition is observed when the substance has a solubility in water at 25° C. of more than 0.05 μg/ml. In a preferred embodiment the substance has a solubility in the range of from 0.05 μg/ml to 0.5 mg/ml, for example from 0.05 μg/ml to 0.05 mg/ml.

The solubility of the substance in water may be measured using a conventional technique. For example, a saturated solution of the substance is prepared by adding an excess amount of the substance to water at 25° C. and allowing the solution to equilibrate for 48 hours. Excess solids are removed by centrifugation or filtration and the concentration of the substance in water is determined by a suitable analytical technique such as HPLC.

Compound of Formula I

Further values of $R^1$, $R^2$, $R^3$, $R^4$ and $R^5$ in compounds of Formula I now follow. It will be understood that such values may be used where appropriate with any of the definitions, claims or embodiments defined hereinbefore or hereinafter.

In one group of compounds of Formula I, $R^1$ represents H, $R^2$ represents cyclohexyl, X is CO and Y is absent.

In a second group of compounds of Formula I, $R^1$ and $R^2$ together with the nitrogen atom to which they are attached represent 1-piperidinyl.

In a third group of compounds of Formula I, $R^1$ represents H and $R^2$ represents phenyl.

A fourth group of compounds of Formula I is represented by formula Ia

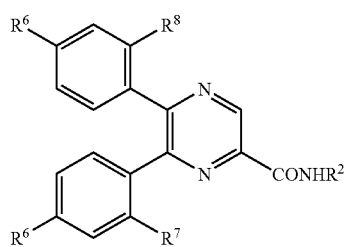

Ia and pharmaceutically acceptable salts, solvates and crystalline forms thereof, in which
$R^2$ represents cyclohexyl, 1-piperidinyl or phenyl;
$R^6$ represents H, chloro, bromo, methyl or methoxy; and
when $R^7$ represents H, $R^8$ represents H or chloro; and
when $R^7$ represents chloro, $R^8$ represents H or chloro.
In a fifth group of compounds of formula I $R^5$ is H.
In a sixth group of compounds of formula I X is CO.
In a seventh group of compounds of formula I X is $SO_2$.
In an eighth group of compounds of formula I Y is absent.

"Pharmaceutically acceptable salt", where such salts are possible, includes both pharmaceutically acceptable acid and base addition salts. A suitable pharmaceutically acceptable salt of a compound of Formula I is, for example, an acid-addition salt of a compound of Formula I which is sufficiently basic, for example an acid-addition salt with an inorganic or organic acid such as hydrochloric, hydrobromic, sulphuric, trifluoroacetic, citric or maleic acid; or, for example a salt of a compound of Formula I which is sufficiently acidic, for example an alkali or alkaline earth metal salt such as a sodium, calcium or magnesium salt, or an ammonium salt, or a salt with an organic base such as methylamine, dimethylamine, trimethylamine, piperidine, morpholine or tris-(2-hydroxyethyl)amine.

Throughout the specification and the appended claims, a given chemical formula or name shall encompass all stereo and optical isomers and racemates thereof as well as mixtures in different proportions of the separate enantiomers, where such isomers and enantiomers exist, as well as pharmaceutically acceptable salts thereof and solvates thereof such as for instance hydrates. Isomers may be separated using conventional techniques, e.g. chromatography or fractional crystallisation. The enantiomers may be isolated by separation of racemate for example by fractional crystallisation, resolution or HPLC. The diastereomers may be isolated by separation of isomer mixtures for instance by fractional crystallisation, HPLC or flash chromatography. Alternatively the stereoisomers may be made by chiral synthesis from chiral starting materials under conditions which will not cause racemisation or epimerisation, or by derivatisation, with a chiral reagent. All stereoisomers are included within the scope of the invention. All tautomers, where possible, are included within the scope of the invention.

The following definitions shall apply throughout the specification and the appended claims.

Unless otherwise stated or indicated, the term "alkoxy" denotes either a straight or branched alkyl group. Examples of said alkyl include methyl, ethyl, n-propyl, isopropyl, n-butyl, iso-butyl, sec-butyl and t-butyl. Preferred alkyl groups are methyl, ethyl, propyl, isopropyl and tertiary butyl.

Unless otherwise stated or indicated, the term "alkoxy" denotes a group O-alkyl, wherein alkyl is as defined above.

Unless otherwise stated or indicated, the term "halogen" shall mean fluorine, chlorine, bromine or iodine.

Specific compounds of the invention are one or more of the following:
N-(1-piperidinyl)-5,6-diphenyl-2-pyrazinecarboxamide;
N-(1-piperidinyl)-5,6-bis(4-bromophenyl)-2-pyrazinecarboxamide;
N-(1-piperidinyl)-5,6-bis(4-methylphenyl)-2-pyrazinecarboxamide;
N-(1-piperidinyl)-5,6-bis(4-methoxyphenyl)-2-pyrazinecarboxamide;
N-(1-piperidinyl)-5,6-bis(4-chlorophenyl)-2-pyrazinecarboxamide;
N-(1-piperidinyl)-5,6-bis(2-chlorophenyl)-2-pyrazinecarboxamide;

N-cyclohexyl-5,6-diphenyl-2-pyrazinecarboxamide;
N-cyclohexyl-5,6-bis(4-bromophenyl)-2-pyrazinecarboxamide;
N-cyclohexyl-5,6-bis(4-methylphenyl)-2-pyrazinecarboxamide;
N-cyclohexyl-5,6-bis(4-methoxyphenyl)-2-pyrazinecarboxamide;
N-cyclohexyl-5,6-bis(4-chlorophenyl)-2-pyrazinecarboxamide;
N-cyclohexyl-5,6-bis(2-chlorophenyl)-2-pyrazinecarboxamide;
N,5,6-triphenyl-2-pyrazinecarboxamide;
N-phenyl-5,6-bis(4-methylphenyl)-2-pyrazinecarboxamide;
N-phenyl-5,6-bis(4-methoxyphenyl)-2-pyrazinecarboxamide;
N-phenyl-5,6-bis(4-chlorophenyl)-2-pyrazinecarboxamide;
N-phenyl-5,6-bis(2-chlorophenyl)-2-pyrazinecarboxamide;
N-(1-piperidinyl)-5-(4-chlorophenyl)-6-(2,4-dichlorophenyl)-2-pyrazinecarboxamide; and
N-(1-piperidinyl)-6-(4-chlorophenyl)-5-(2,4-dichlorophenyl)-2-pyrazinecarboxamide;

and where applicable, optical isomers, tautomers, stereoisomers and racemates thereof as well as pharmaceutically acceptable salts, solvates and crystalline forms thereof.

Methods of Preparation

The compounds of Formula I may be prepared as outlined below according to any of the following methods. The compounds may also be prepared as described for structurally related compounds in the prior art.

Compounds of formula I in which X is CO may be prepared by reacting a compound of formula II

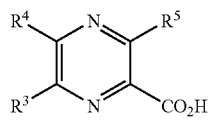

in which $R^3$, $R^4$ and $R^5$ are as previously defined with an amine of formula III

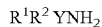

in an inert solvent, for example dichloromethane, in the presence of a coupling agent, for example a carbodimide, eg 1-(3-dimethylaminopropyl)-3-ethylcarbodiimide, and optionally in the presence of a catalyst, for example a basic catalyst, eg 4-dimethylamino-pyridine, at a temperature in the range of $-25°$ C. to $150°$ C.

Compounds of formula I in which X is $SO_2$ may be prepared by reacting a compound of formula IV

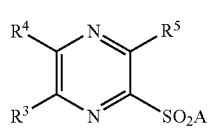

in which $R^3$, $R^4$ and $R^5$ are as previously defined and A represents halo with an amine of formula IV

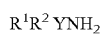

in an inert solvent, for example dichloromethane, and optionally in the presence of a catalyst, for example a basic catalyst, eg 4-dimethylamino-pyridine, at a temperature in the range of $-25°$ C. to $150°$ C.

Compounds of formulae I, III, IV and V may be prepared as described in the Examples and by other methods known to those skilled in the art. Certain compounds of formulae II, III, IV and V are novel and are claimed as a further aspect of the present invention as useful intermediates. Specifically claimed are compounds of formula II in which $R^3$, $R^4$ and $R^5$ are as previously defined with the exception of 5,6-diphenyl-2-pyrazinecarboxylic acid and 5,6-bis(4-methoxyphenyl)-2-pyrazinecarboxylic acid.

The compounds of the invention may be isolated from their reaction mixtures using conventional techniques.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

In the section above the expression "inert solvent" refers to a solvent which does not react with the starting materials, reagents, intermediates or products in a manner which adversely affects the yield of the desired product.

Inhibitor

The inhibitor is a non-polymeric hydrophobic organic compound that is less soluble in water than the substantially water-insoluble substance present in the first solution. Suitable inhibitors have a water solubility at $25°$ C. of less than 0.1 mg/l, more preferably less than 0.01 mg/l. In an embodiment of the invention the inhibitor has a solubility in water at $25°$ C. of less than 0.05 µg/ml, for example from 0.1 ng/ml to 0.05 µg/ml.

In an embodiment of the invention the inhibitor has a molecular weight of less than 2000, such as less than 500, for example less than 400. In another embodiment of the invention the inhibitor has a molecular weight of less than 1000, for example less than 600. For example, the inhibitor may have a molecular weight in the range of from 200 to 2000, preferably a molecular weight in the range of from 400 to 1000, more preferably from 400 to 600.

Suitable inhibitors include an inhibitor selected from classes (i) to (v) or a combination of two or more such inhibitors (for example a mixture of an inhibitor and a co-inhibitor):

(i) a mono-, di- or (more preferably) a tri-glyceride of a fatty acid. Suitable fatty acids include medium chain fatty acids containing from 8 to 12, more preferably from 8 to 10 carbon atoms or long chain fatty acids containing more than 12 carbon atoms, for example from 14 to 20 carbon atoms, more preferably from 14 to 18 carbon atoms. The fatty acid may be saturated, unsaturated or a mixture of saturated and unsaturated acids. The fatty acid may optionally contain one or more hydroxyl groups, for example ricinoleic acid. The glyceride may be prepared by well known techniques, for example, esterifying glycerol with one or more long or medium chain fatty acids. In a preferred embodiment the inhibitor is a mixture of triglycerides obtainable by esterifying glycerol with a mixture of long or, preferably, medium chain fatty acids. Mixtures of fatty acids may be obtained by extraction from natural products, for example from a natural oil such as palm oil. Fatty acids extracted from palm oil contain approximately 50 to 80% by weight decanoic acid and from 20 to 50% by weight of octanoic acid. The use of a mixture of fatty acids to esterify glycerol gives a mixture of glycerides containing a mixture of different acyl chain lengths. Long and medium chain triglycerides are commercially available. For example a preferred medium chain triglyceride (MCT) containing acyl groups with 8 to 12, more preferably 8 to 10 carbon atoms is prepared by esterification of glycerol with fatty acids extracted from palm oil, giving a mixture of triglycerides containing acyl groups with 8 to 12, more preferably 8 to 10 carbon atoms. This MCT is commercially available as Miglyol 812N (Huls, Germany). Other commercially available MCT's include Miglyol 810 and Miglyol 818 (Huls, Germany). A further suitable medium chain triglyceride is trilaurine (glycerol trilaurate). Commercially available long chain trigylcerides include soya bean oil, sesame oil, sunflower oil, castor oil or rape-seed oil.

Mono and di-glycerides may be obtained by partial esterification of glycerol with a suitable fatty acid, or mixture of fatty acids. If necessary the mono- and di-glycerides may be separated and purified using conventional techniques, for example by extraction from a reaction mixture following esterification. When a mono-glyceride is used it is preferably a long-chain mono glyceride, for example a mono glyceride formed by esterification of glycerol with a fatty acid containing 18 carbon atoms;

(ii) a fatty acid mono- or (preferably) di-ester of a $C_{2-10}$ diol. Preferably the diol is an aliphatic diol which may be saturated or unsaturated, for example a $C_{2-10}$-alkane diol which may be a straight chain or branched chain diol. More preferably the diol is a $C_{2-6}$-alkane diol which may be a straight chain or branched chain, for example ethylene glycol or propylene glycol. Suitable fatty acids include medium and long chain fatty acids described above in relation to the glycerides. Preferred esters are di-esters of propylene glycol with one or more fatty acids containing from 8 to 10 carbon atoms, for example Miglyol 840 (Huls, Germany);

(iii) a fatty acid ester of an alkanol or a cycloalkanol. Suitable alkanols include $C_{1-10}$-alkanols, more preferably $C_{2-6}$-alcanols which may be straight chain or branched chain, for example ethanol, propanol, isopropanol, n-butanol, sec-butanol or tert-butanol. Suitable cycloalkanols include $C_{3-6}$-cycloalkanols, for example cyclohexanol. Suitable fatty acids include medium and long chain fatty acids described above in relation to the glycerides. Preferred esters are esters of a $C_{2-6}$-alkanol with one or more fatty acids containing from 8 to 10 carbon atoms, or more preferably 12 to 29 carbon atoms, which fatty acid may saturated or unsaturated. Suitable esters include, for example isopropyl myristrate or ethyl oleate;

(iv) a wax. Suitable waxes include esters of a long chain fatty acid with an alcohol containing at least 12 carbon atoms. The alcohol may an aliphatic alcohol, an aromatic alcohol, an alcohol containing aliphatic and aromatic groups or a mixture of two or more such alcohols. When the alcohol is an aliphatic alcohol it may be saturated or unsaturated. The aliphatic alcohol may be straight chain, branched chain or cyclic. Suitable aliphatic alcohols include those containing more than 12 carbon atoms, preferably more than 14 carbon atoms especially more than 18 carbon atoms, for example from 12 to 40, more preferably 14 to 36 and especially from 18 to 34 carbon atoms. Suitable long chain fatty acids include those described above in relation to the glycerides, preferably those containing more than 14 carbon atoms especially more than 18 carbon atoms, for example from 14 to 40, more preferably 14 to 36 and especially from 18 to 34 carbon atoms. The wax may be a natural wax, for example bees wax, a wax derived from plant material, or a synthetic wax prepared by esterification of a fatty acid and a long chain alcohol. Other suitable waxes include petroleum waxes such as a paraffin wax;

(v) a long chain aliphatic alcohol. Suitable alcohols include those with 6 or more carbon atoms, more preferably 8 or more carbon atoms, such as 12 or more carbon atoms, for example from 12 to 30, for example from 14 to 20 carbon atoms. It is especially preferred that the long chain aliphatic alcohol has from 6 to 20, more especially from 6 to 14 carbon atoms, for example from 8 to 12 carbon atoms. The alcohol may be straight chain, branched chain, saturated or unsaturated. Examples of suitable long chain alcohols include, 1-hexanol, 1-decanol, 1-hexadecanol, 1-octadecanol, or 1-heptadecanol (more preferably 1-decanol); or (vi) a hydrogenated vegetable oil, for example hydrogenated castor oil.

In one embodiment of the present invention the inhibitor is selected from a medium chain triglyceride and a long chain aliphatic alcohol containing from 6 to 12, preferably from 10 to 20 carbon atoms. Preferred medium chain triglycerides and long chain aliphatic alcohols are as defined above. In a preferred embodiment the inhibitor is selected from a medium chain triglyceride containing acyl groups with from 8 to 12 carbon atoms or a mixture of such triglycerides (preferably Miglyol 812N) and an aliphatic alcohol containing from 10 to 14 carbon atoms (preferably 1-decanol) or a mixture thereof (for example a mixture comprising Miglyol 812N and 1-decanol).

Suitably the inhibitor is a liquid at the temperature at which the dispersion is prepared. Preferably the inhibitor is liquid at ambient temperature (25° C.).

When the substantially water-insoluble substance is a pharmacologically active compound the inhibitor is preferably a pharmaceutically inert material.

The inhibitor is present in the particles in a quantity sufficient to prevent Ostwald ripening of the particles in the suspension. Preferably the inhibitor will be the minor component in the solid particles formed in the present process comprising the inhibitor and the substantially water-insoluble substance. Preferably, therefore, the inhibitor is present in a quantity that is just sufficient to prevent Ostwald ripening of the particles in the dispersion, thereby minimising the amount of inhibitor present in the particles.

In embodiments of the present invention the weight fraction of inhibitor relative to the total weight of inhibitor and substantially water-insoluble substance (i.e. weight of inhibitor/weight of inhibitor+weight of substantially water-insoluble substance) is from 0.01 to 0.99, preferably from 0.01 to 0.5, especially from 0.05 to 0.3 and more especially from 0.06 to 0.25. In a preferred embodiment the weight fraction of inhibitor relative to the total weight of inhibitor and substantially water-insoluble substance is less than 0.5, more preferably 0.3 or less, for example from 0.05 to 0.3, such as from 0.06 to 0.25, for example about 0.2. This is particularly preferred when the substantially water-insoluble substance is a pharmacologically active substance because high levels of inhibitor (e.g. a weight fraction above 0.5) may give rise to unwanted side effects and/or affect the dissolution rate/bioavailability of the pharmacologically active substance when administered in vivo.

Furthermore, we have found that in general a low weight ratio of inhibitor to the inhibitor and the substantially water-insoluble substance which is a compound of Formula I (i.e. less than 0.5) is sufficient to prevent particle growth by Ostwald ripening, thereby allowing small (preferably less than 1 µm, preferably less than 500 nm) stable particles to be prepared. A small and constant particle size is often desirable, especially when the substantially water-insoluble substance is a pharmacologically active material that is used, for example, for intravenous administration.

One application of the dispersions prepared by the process according to the present invention is the study of the toxicology of compounds of Formula I. The dispersions prepared according to the present process can exhibit improved bioavailability compared to dispersions prepared using alternative processes, particularly when the particle size of the substance is less than 0.5 µm. In this application it is advantageous to minimise the amount of inhibitor relative to the active compound so that any effects on the toxicology associated with the presence of the inhibitor are minimised.

When the substantially water-insoluble substance has an appreciable solubility in the inhibitor the weight ratio of inhibitor to substantially water-insoluble substance should be selected to ensure that the amount of substantially water-insoluble substance exceeds that required to form a saturated solution of the substantially water-insoluble substance in the inhibitor. This ensures that solid particles of the substantially water-insoluble substance are formed in the dispersion. This is important when the inhibitor is a liquid at the temperature at which the dispersion is prepared (for example ambient temperature) to ensure that the process does not result in the formation liquid droplets comprising a solution of the substantially water-insoluble substance in the inhibitor, or a two phase system comprising the solid substance and large regions of the liquid inhibitor.

Without wishing to be bound by theory we believe that systems in which there is a phase separation between the substance and inhibitor in the particles are more prone to Ostwald ripening than those in which the solid particles form a substantially single phase system. Accordingly, in a preferred embodiment the inhibitor is sufficiently miscible in the substantially water-insoluble material to form solid particles in the dispersion comprising a substantially single-phase mixture of the substance and the inhibitor. The composition of the particles formed according to the present invention may be analysed using conventional techniques, for example analysis of the (thermodynamic) solubility of the substantially water-insoluble substance in the inhibitor, melting entropy and melting points obtained using routine differential scanning calorimetry (DSC) techniques to thereby detect phase separation in the solid particles. Furthermore, studies of nano-suspensions using nuclear magnetic resonance (NMR) (e.g. line broadening of either component in the particles) may be used to detect phase separation in the particles.

Generally the inhibitor should have a sufficient miscibility with the substance to form a substantially single phase particle, by which is meant that the inhibitor is molecularly dispersed in the solid particle or is present in small domains of inhibitor dispersed throughout the solid particle. It is thought that for many substances the substance/inhibitor mixture is a non-ideal mixture by which is meant that the mixing of two components is accompanied by a non-zero enthalpy change.

An indication of the substance/inhibitor miscibility in the solid particles is provided by the interaction parameter $\chi$ for the substance-inhibitor mixture. The $\chi$ parameter may be derived from the well known Bragg-Williams, Flory-Huggins or the Regular Solution theories (see e.g. Jönsson, B. Lindman, K. Holnberg, B. Kronberg, "Surfactants and Polymers in Solution", John Wiley & Sons, 1998 and Neau et al, Pharmaceutical Research, 14, 601 1997). In an ideal mixture $\chi$ is 0, and according to the Bragg-Williams theory a two-component mixture will not phase separate provided $\chi<2$. We believe that in many particles prepared according to the present invention the substance and inhibitor are not ideal mixtures and therefore the $\chi$ value is not zero.

We have surprisingly found that when $\chi$ is <2.5 the solid particles prepared according to the invention exhibit little or no Ostwald ripening. Those systems in which $\chi$ is >2.5 are thought to be prone to phase separation and are less stable to Ostwald ripening. Suitably the $\chi$ value of the substance-inhibitor mixture is 2 or less, for example from 0 to 2, preferably 0.1 to 2, such as 0.2 to 1.8.

Many small molecule organic substances (Mw<1000) are available in a crystalline form or can be prepared in crystalline form using conventional techniques (for example by recrystallisation from a suitable solvent system). In such cases the $\chi$ parameter of the substance and inhibitor mixture is easily determined from the Equation I:

$$\chi = \frac{-\Delta S_m \ln[T_m/T]R - \ln x_1^s}{(1-x_1^s)^2} \qquad \text{Equation I}$$

wherein:

$\Delta S_m$ is the entropy of melting of the crystalline substantially water-insoluble substance (measured using a conventional technique such as DSC measurement);

$T_m$ is the melting point (K) of the crystalline substantially water-insoluble substance (measured using a conventional technique such as DSC measurement);

T is the temperature of the dispersion (K);

R is the gas constant; and $x_1^s$ is the mole fraction solubility of the crystalline substantially water-insoluble substance in the inhibitor (measured using conventional techniques for determining solubility for example as hereinbefore described). In the above equation $T_m$ and $\Delta S_m$ refer to the melting point of the crystalline form of the material. In those cases where the substance may exist in the form of different polymorphs, $T_m$ and $\Delta S_m$ are determined for the polymorphic form of the substance that is most stable at the temperature of the dispersion. As will be understood, the measurement of $\Delta S_m$, and $x_1^s$ are performed on the crystalline substantially water-insoluble substance prior to formation of the dispersion according to the invention and thereby enables a preferred inhibitor for the substantially water-insoluble material to be selected by performing simple measurements on the bulk crystalline material.

The mole fraction solubility of the crystalline substantially water-insoluble substance in the inhibitor ($x_1^s$) is simply the number of moles of substance per mole of inhibitor present in a saturated solution of the substance in the inhibitor. As will be realized the equation above is derived for a two component system of a substance and an inhibitor. In those systems where the inhibitor contains more than one compound (for example in the case of a medium chain triglyceride comprising a mixture of triglycerides such as Miglyol 812N, or where a mixture of inhibitors is used) it is sufficient to calculate $x_1^s$ in terms of the "apparent molarity" of the mixture of inhibitors. The apparent molarity of such a mixture is calculated for a mixture of n inhibitor components to be:

$$\text{Apparent molarity} = \frac{\text{Mass of 1 litre of inhibitor mixture}}{[(a*Mwa) + (b*Mwb) + \ldots (n*Mwn)]}$$

wherein: a, b . . . n are the weight fraction of each component in the inhibitor mixture (for example for component a this is % w/w component a/100); and Mwa . . . . Mwn is the molecular weight of each component a. n in the mixture.

$x^s_1$ is then calculated as:

$$x^s_1 = \frac{\text{Molar solubility of the crystalline substance in the inhibitor mixture (mol/l)}}{\text{Apparent molarity of inhibitor mixture (mol/l)}}$$

When the inhibitor is a solid at the temperature that the dispersion is prepared, the mole fraction solubility, $x^s_1$, can be estimated by measuring the mole fraction solubility at a series of temperatures above the melting point of the inhibitor and extrapolating the solubility back to the desired temperature. However, as hereinbefore mentioned, it is preferred that the inhibitor is a liquid at the temperature that the dispersion is prepared. This is advantageous because, amongst other things, the use of a liquid inhibitor enables the value of $x^s_1$ to be measured directly.

In certain cases, it may not be possible to obtain the substantially water-insoluble material in a crystalline form. In such cases, preferred inhibitors are those which are sufficiently miscible with the substantially water-insoluble material to form a substantially single phase mixture when mixed in the required substance:inhibitor ratio. Miscibility of the inhibitor in the substantially water-insoluble material may be determined using routine experimentation. For example the substance and inhibitor may be dissolved in a suitable organic solvent followed by removal of the solvent to leave a mixture of the substance and inhibitor. The resulting mixture may then be characterised using a routine technique such as DSC characterisation to determine whether or not the mixture is a single phase system. This empirical method enables preferred inhibitors for a particular substance to be selected and will provide substantially single phase solid particles in the dispersion prepared according to the present invention.

In a further embodiment of the present invention the miscibility of the substance and the inhibitor may be increased by the addition of a suitable co-inhibitor to the first solution in the present process. The presence of the co-inhibitor increases the miscibility of the substance and the inhibitor mixture, thereby reducing the $\chi$ value and further reducing or preventing Ostwald ripening. Suitable co-inhibitors include an inhibitor as hereinbefore defined, preferably an inhibitor selected from classes (i) to (v) listed hereinbefore. In a preferred embodiment when the inhibitor is a medium chain triglyceride containing acyl groups with 8 to 12 carbon atoms (or a mixture of such triglycerides such as Miglyol 812N), a preferred co-inhibitor is a long chain aliphatic alcohol containing 6 or more carbon atoms (preferably from 6 to 14 carbon atoms) for example 1-hexanol or more preferably 1-decanol. The weight ratio of inhibitor:co-inhibitor is selected to give the desired $\chi$ value of the substance/inhibitor/co-inhibitor mixture and may be varied over wide limits, for example from 10:1 to 1:10, such as approximately 1:1. Preferred values for $\chi$ are as hereinbefore defined.

The inhibitor in the present invention is not a phospholipid. Such lipids have a hydrophilic phosphorous containing "head" groups and one or more lipophilic "tail" groups. Such phosphlipids are capable of forming lipid bilayers and exhibit surface-active effects. Examples of phospholipids excluded from the present invention include, for example the phospholipids described in U.S. Pat. No. 5,100,591.

Water-Miscible Organic Solvent

The water-miscible organic solvent in the first phase is preferably miscible with water in all proportions. The water-miscible organic solvent should also be a solvent for both the substantially water-insoluble substance and the inhibitor. The water-miscible organic solvent is selected such that the inhibitor and the substantially water-insoluble substance each have a sufficient solubility in the water miscible organic solvent to enable a precipitate of the substantially water-insoluble substance to form when the first solution is combined with the aqueous phase. Suitably, the inhibitor and the substantially water-insoluble substance each have a solubility of 10 mg/ml or more in the water-miscible organic solvent.

Generally it is preferred that the concentration of the substantially water-insoluble substance in the water-miscible organic solvent is as high as possible to aid efficient precipitation. The upper concentration of the substantially water-insoluble substance in the water-miscible organic solvent is determined by the solubility of the substance in the solvent.

However, we have found that a wide range of concentrations may be used in the present process. Typically, a concentration of substantially water-insoluble substance of 1% by weight or more in the organic solvent is sufficient.

The inhibitor and/or the substantially water-insoluble substance should be completely dissolved in the water-miscible organic solvent. The presence of particles of the inhibitor and/or the substantially water-insoluble substance in the first solution may result in poor control of the particle size distribution in the dispersion.

If required the solubility of the inhibitor and/or the substantially water-insoluble substance in the water-miscible organic solvent can be increased by heating a mixture of the inhibitor, substantially water-insoluble substance and water-miscible organic solvent to provide a solution. The solution is then maintained at elevated temperature until it is combined with the aqueous phase in the process.

As will be understood, the selection of water-miscible organic solvent will be dependent upon the nature of the substantially water-insoluble substance. When the substantially water-insoluble substance is an organic compound the water-miscible organic solvent should have a sufficiently low dielectric constant to be able to dissolve the substantially water-insoluble substance and the inhibitor. Suitable water-miscible solvents for dissolving a substantially water-insoluble organic substance include, a water-miscible alcohol, for example methanol, ethanol, n-propyl alcohol, isopropyl alcohol, tert-butyl alcohol, ethylene glycol or propylene glycol; dimethylsulfoxide; dimethylformamide; a water-miscible ether, for example tetrahydrofuran; a water-miscible nitrile, for example acetonitrile; a water-miscible ketone, for example acetone or methyl ethyl ketone; an amide, for example dimethylacetamide or a mixture of two or more of the above mentioned water-miscible organic solvents. A preferred water-miscible organic solvent is dimethylacetamide (DMA).

Precipitation

In the present process the first solution and the aqueous phase may be combined by adding the first solution to the aqueous phase. Alternatively, the aqueous phase may be added to the first solution. During the combination of the first solution and the aqueous phase the conditions are controlled to give precipitated solid particles of the required particle size. The particle size resulting from the combination of the first solution and aqueous phase is determined by a number of factors including, the rate of agitation during the combination of the first solution and the aqueous phase, the temperature during the combination and the rate at which the combination takes place. As will be clear, sufficient aqueous phase is used during the combination to extract sufficient water-miscible organic solvent from the first solution to cause precipitation of the solid particles from the first solution.

Suitable conditions for the addition of the aqueous phase to the first solution for the formation of sub-micron particles are described in U.S. Pat. No. 4,826,689, incorporated herein by reference thereto, wherein an aqueous phase is injected into an agitated phase containing the substance dissolved in an organic solvent. Suitable rates of addition are typically from 100 ml/min to 1000 ml/min per 50 ml of the first solution. A suitable temperature for the addition is from 0 to 100° C., more preferably from 5 to 50° C.

Addition of the aqueous phase into the first solution may be achieved using a number of techniques, for example by injecting the aqueous phase directly into the first solution (for example via a syringe) or by adding the aqueous phase dropwise into the first solution. For larger scale production the aqueous phase may be added to the first solution using a flow mixer. Preferably the first solution is agitated during addition of the aqueous phase by for example stirring, preferably at a rate sufficient to induce a high degree of turbulence in the first solution and hence a very rapid precipitation and distribution of particles into the liquid medium of the dispersion. Alternatively, the first solution may be agitated by sonication in an ultrasonic bath.

When the first solution is added to the aqueous phase, the aqueous phase is preferably agitated as described above, thereby enhancing extraction of water-miscible solvent from the first solution to give small particles and good dispersion of the particles in the liquid medium. Suitable rates and methods of addition, temperature and degree of agitation are analogous to those described above for the addition of the aqueous phase into the first solution.

Some particles will precipitate and form a uniform dispersion without the need for a stabiliser in the aqueous phase. However, we have found that many particles tend to aggregate upon precipitation unless a stabiliser is present in the aqueous phase.

Stabilisers suitable for the prevention of particle aggregation in dispersions are well known to those skilled in the art. Suitable stabilisers include dispersants and surfactants (which may be anionic, cationic or non-ionic) or a combination thereof. Suitable dispersants include, a polymeric dispersant, for example a polyvinylpyrrolidone, a polyvinylalcohol or a cellulose derivative, for example hydroxypropylmethyl cellulose, hydroxy ethyl cellulose, ethylhydroxyethyl cellulose or carboxymethyl cellulose. Suitable anionic surfactants include alkyl and aryl sulphonates, sulphates or carboxylates, such as an alkali metal alkyl and aryl sulphonate or sulphate, for example, sodium dodecyl sulphate. Suitable cationic surfactants include quaternary ammonium compounds and fatty amines. Suitable non-ionic surfactants include, monoesters of sorbitan which may or may not contain a polyoxyethylene residue, ethers formed between fatty alcohols and polyoxyethylene glycols, polyoxyetheylene-polypropylene glycols, an ethoxylated castor oil (for example Cremophor EL), ethoxylated hydrogenated castor oil, ethoxylated 12OH-stearic acid (for example Solutol HS15). The aqueous phase may contain a single stabiliser or a mixture of two or more stabilisers. In a preferred embodiment the aqueous phase contains a polymeric dispersant and a surfactant (preferably an anionic surfactant), for example a polyvinylpyrrolidone and sodium dodecyl sulphate. When the substantially water-insoluble material is a pharmacologically active compound it is preferred that the stabiliser is a pharmaceutically acceptable material.

Generally the aqueous phase will contain from 0.01 to 1% by weight, preferably from 0.05 to 0.5% by weight and especially from 0.1 to 0.2% by weight of stabiliser. We have found that the dispersions prepared according to the present process require lower levels of stabilisers (such as surfactants) compared to precipitation processes that do not use an inhibitor.

Optionally, additional stabiliser may be added to the dispersion after precipitation of the particles into the aqueous phase to provide additional inhibition of particle aggregation in the dispersion.

The combination of the first solution and aqueous phase in the process according to the present invention results in very fast, substantially instantaneous precipitation of particles of the inhibitor and substantially water-insoluble material to give particles of the desired size with a narrow particle size distribution. The precipitation avoids the need to form an emulsion prior to extraction of the water-miscible organic solvent, and thereby considerably simplifies the preparation of a dispersion of solid particles compared to emulsion-based processes.

Optionally the water-miscible organic solvent can be removed from the dispersion after the precipitation. Suitable methods for removing the water-miscible organic solvent include evaporation, for example by heating the dispersion under vacuum, reverse osmosis, dialysis, ultra-filtration or cross-flow filtration. The dispersion may be concentrated after precipitating the particles by removing excess water from the dispersion, for example by evaporation, spray drying or lyophilisation.

Optionally additional components may be added to the dispersion for example viscosity modifying agents, buffers, taste masking agents, anti-oxidants, preservatives or colorants. The additional components may be added before, or more preferably, after the precipitation of the particles.

According to a further embodiment of the present invention there is provided a process for the preparation of a stable dispersion of solid particles of a substantially water-insoluble substance which is a compound of Formula I in an aqueous medium comprising:

combining (a) a first solution comprising the substantially water-insoluble compound of Formula I, a water-miscible organic solvent and an inhibitor with (b) an aqueous phase comprising water and optionally a stabiliser, thereby precipitating solid particles comprising the inhibitor and the substantially water-insoluble pharmacologically active substance; and optionally removing the water-miscible organic solvent;

wherein the inhibitor is less soluble in water than the pharmacologically active substance, which inhibitor is selected from one or more of:
   (i) a mono-, di- or (more preferably) a tri-glyceride of a fatty acid;
   (ii) a fatty acid mono- or (preferably) di-ester of a $C_{2-10}$ diol;
   (iii) a fatty acid ester of an alkanol or a cycloalkanol;

(iv) a wax;
(v) a long chain aliphatic alcohol (preferably containing 6 or more carbon atoms, for example from 8 to 12 carbon atoms); and
(vi) a hydrogenated vegetable oil.

This embodiment of the present invention provides stable dispersions of particles of a solid substantially water-insoluble substance which is a compound of Formula I in an aqueous medium. The dispersions prepared according to this embodiment exhibit little or no growth in particle size during storage (resulting from, Ostwald ripening).

In this embodiment it is preferred that the miscibility of the substantially water-insoluble substance and inhibitor are sufficient to give substantially single phase solid particles in the dispersion, more preferably the inhibitor/substance mixture has a $\chi$ value of <2.5, more preferably 2 or less, for example from 0 to 2, preferably from 0.1 to 2 wherein the $\chi$ value is as hereinbefore defined.

In this embodiment the inhibitor is preferably a medium chain tri-glyceride (MCT) containing acyl groups with 8 to 12 (more preferably 8 to 10) carbon atoms, or a mixture thereof, for example Miglyol 812N. The miscibility of the inhibitor with the substance may be increased by using a co-inhibitor as hereinbefore described. For example, a suitable inhibitor/co-inhibitor in this embodiment comprises a medium chain tri-glyceride (MCT) as defined above and a long chain aliphatic alcohol having 6 to 12 (more preferably 8 to 12, for example 10) carbon atoms, or a mixture comprising two or more such inhibitors (for example 1-hexanol or (more preferably) 1-decanol). A preferred inhibitor/co-inhibitor for use in this embodiment is a mixture of Miglyol 812N and 1-decanol.

If required the particles present in the dispersion prepared according to the present invention may be isolated from the aqueous medium following precipitation (or removal of the water-miscible organic solvent, if used). The particles may be separated using conventional techniques, for example by centrifuging, reverse osmosis, membrane filtration, lyophilisation or spray drying. Isolation of the particles is useful when the particles comprise a substantially water-insoluble pharmacologically active compound of Formula I because it allows the particles to be washed and re-suspended in a sterile aqueous medium to give a suspension suitable for administration to a warm blooded mammal (especially a human), for example by oral or parenteral (e.g. intravenous) administration.

In this embodiment an agent may be added to the suspension prior to isolation of the particles to prevent agglomeration of the solid particles during isolation (for example spray drying or lyophilisation). Suitable agents include for example a sugar such as mannitol. Isolation of the particles from the suspension is also useful when it is desirable to store the particles as a powder. The powder may then be re-suspended in an aqueous medium prior to use. This is particularly useful when the substantially water-insoluble substance is a pharmacologically active compound of Formula I. The isolated particles of the substance may then be stored as a powder in, for example a vial and subsequently be re-suspended in a suitable liquid medium for administration to a patient as described above.

Alternatively the isolated particles may be used to prepare solid formulations, for example by blending the particles with suitable excipients/carriers and granulating or compressing the resulting mixture to form a tablet or granules suitable for oral administration. Alternatively the particles may be suspended, dispersed or encapsulated in a suitable matrix system, for example a biocompatible polymeric matrix, for example a hydroxypropyl methylcellulose (HPMC) or polylactide/glycloide polymer to give a controlled or sustained release formulation.

In another embodiment of the present invention the process is performed under aseptic conditions, thereby providing a sterile dispersion directly which can be administered to a warm blooded mammal as described above without the need for additional purification or sterilisation steps. Alternatively, the dispersion may be sterile filtered following precipitation and optional removal of the water-miscible organic solvent to leave a sterile suspension.

According to a further aspect of the present invention there is provided a stable aqueous dispersion comprising a continuous aqueous phase in which is dispersed solid particles comprising an inhibitor and a substantially water-insoluble substance which is a compound of Formula I, wherein said dispersion is obtainable by the process according to the present invention; and wherein:
(i) the inhibitor is a non-polymeric hydrophobic organic compound that is substantially insoluble in water;
(ii) the inhibitor is less soluble in water than the substantially water-insoluble substance; and
(iii) the inhibitor is not a phospholipid.

The dispersion according to this aspect of the present invention exhibit little or no particle growth upon storage, mediated by Ostwald ripening (i.e. the dispersion is a stable dispersion as defined above in relation to the first aspect of the invention).

The particles preferably have a mean diameter of less than 1 μm and more preferably less than 500 nm. It is especially preferred that the particles in the dispersion have a mean particle size of from 10 to 500 nm, more especially from 50 to 300 nm and still more especially from 100 to 200 nm.

The weight fraction of inhibitor in the particles is preferably less than 0.5, more preferably 0.3 or less, for example from 0.05 to 0.3, preferably from 0.06 to 0.25.

It is preferred that the miscibility of the substantially water-insoluble material and inhibitor are sufficient to give substantially single phase solid particles, more preferably the inhibitor/substance mixture has a $\chi$ value of <2.5, more preferably 2 or less, for example from 0 to 2, preferably from 0.1 to 2, wherein the $\chi$ value is as hereinbefore defined.

The particles may contain a single compound of Formula I or two or more such substances. The particles may contain a single inhibitor or a combination of an inhibitor and one or more co-inhibitors as hereinbefore described.

The dispersions according to the present invention may be administered to a warm blooded mammal (especially a human), for example by oral or parenteral (e.g. intravenous) administration. In an alternative embodiment the dispersion may be used as a granulation liquid in a wet granulation process to prepare granules comprising the substantially water-insoluble pharmacologically active material and one or more excipients (optionally after first concentrating the dispersion by removal of excess aqueous medium). The resulting granules may then be used directly, for example by filling into capsules to provide a unit dosage containing the granules. Alternatively the granules may be optionally mixed with further excipients, disintegrants, binders, lubricants etc. and compressed into a tablet suitable for oral administration. If required the tablet may be coated to provide control over the release properties of the tablet or to protect it against degradation, for example through exposure to light and/or moisture. Wet granulation techniques and excipients suitable for use in tablet formulations are well known in the art.

According to a further aspect of the present invention there is provided a solid particle comprising an inhibitor and a substantially water-insoluble substance which is a compound of Formula I obtainable by the process according to the present invention, wherein the substance and the inhibitor are as hereinbefore defined in relation to the first aspect of the present invention.

According to a further aspect of the present invention there is provided a solid particle comprising an inhibitor and a substantially water-insoluble substance which is a compound of Formula I obtainable by the process according to the present invention, for use as a medicament, According to a further aspect of the present invention there is provided a pharmaceutical composition comprising a pharmaceutically acceptable carrier or diluent in association with a solid particle comprising an inhibitor and a substantially water-insoluble pharmacologically active substance which is a compound of Formula I obtainable by the process according to the present invention.

Suitable pharmacutically acceptable carriers or diluents are well known excipients used in the preparation of pharmaceutical formulations, for example, fillers, binders, lubricants, disintegrants and/or release controlling/modifying excipients.

According to a further aspect of the present invention there is provided a method for inhibiting Ostwald ripening in a dispersion of solid substantially water-insoluble particles in an aqueous medium comprising:

combining (a) a first solution comprising a substantially water-insoluble substance which is a compound of Formula I, a water-miscible organic solvent and an inhibitor with (b) an aqueous phase comprising water and optionally a stabiliser, thereby precipitating solid particles comprising the inhibitor and the substantially water-insoluble substance to give a dispersion of the solid substantially water-insoluble particles in an aqueous medium; and optionally removing the water-miscible organic solvent from the dispersion;
wherein:
(i) the inhibitor is a non-polymeric hydrophobic organic compound that is substantially insoluble in water;
(ii) the inhibitor is less soluble in water than the substantially water-insoluble substance; and
(iii) the inhibitor is not a phospholipid.

Preferred inhibitors and substantially water-insoluble substances for use in this embodiment are as hereinbefore defined in relation to the first aspect of the present invention.

According to a further aspect of the present invention there is provided the use of an inhibitor to prevent or inhibit Ostwald ripening in a dispersion of solid substantially water-insoluble particles in an aqueous medium wherein:
(i) the inhibitor is a non-polymeric hydrophobic organic compound that is substantially insoluble in water;
(ii) the inhibitor is less soluble in water than the substantially water-insoluble substance; and
(iii) the inhibitor is not a phospholipid.

Preferred inhibitors and substantially water-insoluble substances for use in this embodiment are as hereinbefore defined in relation to the first aspect of the present invention.

The invention is further illustrated by the following examples in which all parts are parts by weight unless stated otherwise.

Particle sizes are quoted as the intensity-averaged particle size determined by dynamic light scattering using a Coulter N4MD.

Pharmacological Properties

The dispersions and particles of the present invention are useful for the treatment of obesity, psychiatric disorders such as psychotic disorders, schizophrenia, bipolar disorders, anxiety, anxio-depressive disorders, depression, cognitive disorders, memory disorders, obsessive-compulsive disorders, anorexia, bulimia, attention disorders like ADHD, epilepsy, and related conditions, and neurological disorders such as dementia, neurological disorders (e.g. Multiple Sclerosis), Raynaud's syndrome, Parkinson's disease, Huntington's chorea and Alzheimer's disease. The dispersions and particles of the present invention are also potentially useful for the treatment of immune, cardiovascular, reproductive and endocrine disorders, septic shock and diseases related to the respiratory and gastrointestinal systems (e.g. diarrhea). The dispersions and particles of the present invention are also potentially useful as agents in treatment of extended abuse, addiction and/or relapse indications, e.g. treating drug (nicotine, ethanol, cocaine, opiates, etc) dependence and/or treating drug (nicotine, ethanol, cocaine, opiates, etc) withdrawal symptoms. The dispersions and particles of the present invention may also eliminate the increase in weight which normally accompanies the cessation of smoking.

In a further aspect the present invention provides the use of a dispersion of a compound of formula I in the preparation of a medicament for the treatment or prophylaxis of obesity, psychiatric disorders such as psychotic disorders, schizophrenia, bipolar disorders, anxiety, anxio-depressive disorders, depression, cognitive disorders, memory disorders, obsessive-compulsive disorders, anorexia, bulimia, attention disorders like ADHD, epilepsy, and related conditions, neurological disorders such as dementia, neurological disorders (e.g. Multiple Sclerosis), Parkinson's Disease, Huntington's Chorea and Alzheimer's Disease, immune, cardiovascular, reproductive and endocrine disorders, septic shock, diseases related to the respiratory and gastrointestinal systems (e.g. diarrhea), and extended abuse, addiction and/or relapse indications, e.g. treating drug (nicotine, ethanol, cocaine, opiates, etc) dependence and/or treating drug (nicotine, ethanol, cocaine, opiates, etc) withdrawal symptoms.

In a still further aspect the present invention provides a method of treating obesity, psychiatric disorders such as psychotic disorders such as schizophrenia and bipolar disorders, anxiety, anxio-depressive disorders, depression, cognitive disorders, memory disorders, obsessive-compulsive disorders, anorexia, bulimia, attention disorders like ADHD, epilepsy, and related conditions, neurological disorders such as dementia, neurological disorders (e.g. Multiple Sclerosis), Parkinson's Disease, Huntington's Chorea and Alzheimer's Disease, immune, cardiovascular, reproductive and endocrine disorders, septic shock, diseases related to the respiratory and gastrointestinal systems (e.g. diarrhea), and extended abuse, addiction and/or relapse indications, e.g. treating drug (nicotine, ethanol, cocaine, opiates, etc) dependence and/or treating drug (nicotine, ethanol, cocaine, opiates, etc) withdrawal symptoms comprising administering a pharmacologically effective amount of a compound of formula I as a dispersion and or as particles of the present invention to a patient in need thereof.

The dispersions and particles of the present invention of the present invention are particulary suitable for the treatment of obesity, e.g. by reduction of appetite and body weight, maintenance of weight reduction and prevention of rebound.

EXAMPLE 1

5,6-bis(4-chlorophenyl)-N-piperidin-1-ylpyrazine-2-carboxamide/Miglyol 812 N (4:1 w/w) Dispersion A solution of 300 mM 5,6-bis(4-chlorophenyl)-N-piperidin-1-ylpyrazine-2-carboxamide and 32.1 mg/ml Miglyol 812N in dimethylacetamide (DMA) was prepared. 0.15 ml of this solution was added rapidly to 2.85 ml of an aqueous solution containing 0.2% w/w polyvinylpyrrolidone (PVP) and 0.25 mM sodium dodecyl sulfate (SDS). The aqueous solution was sonicated during the addition of the organic solution using an ultrasonic bath. This resulted in the precipitation of particles with a mean size of 165 nm, as measured by dynamic light scattering using a Coulter N4MD. No increase in particle size was observed over a period of 2 hours, at 20° C.

Preparation of Compounds of Formula I

ABBREVIATIONS

DCM—dichloromethane
DMF—dimethylformamide
DMAP—4-dimethylaminopyridine
EDC—1-(3-dimethylaminopropyl)-3-ethylcarbodiimide
TEA—triethylamine
TFA—trifluoroacetic acid
DMSO-dimethyl sulfoxide
DEA—Diethylamine
PCC—Pyridinium chlorochromate
DCM—Dichloromethane
t triplet
s singlet
d doublet
q quartet
qvint quintet
m multiplet
br broad
bs broad singlet
dm doublet of multiplet
bt broad triplet
dd doublet of doublet General Experimental Procedures Mass spectra were recorded on either a Micromass ZQ single quadrupole or a Micromass LCZ single quadrupole mass spectrometer both equipped with a pneumatically assisted electrospray interface (LC-MS). $^1$H NMR measurements were performed on either a Varian Mercury 300 or a Varian Inova 500, operating at $^1$H frequencies of 300 and 500 MHz respectively. Chemical shifts are given in ppm with $CDCl_3$ as internal standard. Purification was performed on a semipreparative HPLC with a mass triggered fraction collector, Shimadzu QP 8000 single quadrupole mass spectrometer equipped with 19×100 mm C8 column. The mobile phase used was, if nothing else is stated, acetonitrile and buffer (0.1 M $NH_4Ac$:acetonitrile 95:5).

For isolation of isomers, a Kromasil CN E9344 (250×20 mm i.d.) column was used. Heptane:ethyl acetate:DEA 95:5: 0.1 was used as mobile phase (1 ml/min). Fraction collection was guided using a UV-detector (330 nm).

Synthesis of Intermediates

The following intermediates were not commercially available and therefore prepared as described in Preparation A, (Chem. Ber., 100, 1967, p. 555).

Preparation A (a) 5,6-diphenyl-pyrazine-2-carboxylic acid

The monohydrochloride of 2,3-diaminopropionic acid (500 mg, 3.56 mmol) and benzil (890 mg, 4.23 mmol) were added to a solution of sodium hydroxide (677 mg, 16.93 mmol) in methanol (10 ml). An extra portion of methanol was added (5 ml) and the reaction mixture was refluxed for 20 minutes. The mixture was cooled to 25° C. and air was bubbled through for 30 minutes. Hydrochloric acid (aq, 2 M) was added until the reaction mixture reached pH 2. The solution was extracted with diethyl ether. The combined diethyl ether phases were dried ($MgSO_4$), filtrated and evaporated under reduced pressure to give the crude product. MS m/z 277 $(M+H)^+$. The crude product was used in steps described below without further purification.

(b) 5,6-Bis-(4-bromophenyl)-pyrazine-2-carboxylic acid

The title compound was prepared essentially as described in Preparation A step (a), using monohydrochloride of 2,3-diaminopropionic acid (600 mg, 4.26 mmol) and 4,4'-dibromobenzil (1.745 g, 4.26 mmol, 90%) as starting materials. The reaction mixture was refluxed for 2 hours and air was bubbled through for 1 hour. Hydrochloric acid (aq, 2 M) was added until pH 2. The mixture was evaporated under reduced pressure and the residue was dissolved in water. The solution was extracted with diethyl ether, the combined diethyl ether phases were dried ($MgSO_4$), filtered and evaporated under reduced pressure. The crude product (500 mg, 27%) was used in steps described below without further purification. MS m/z 435, 437, 439 $(M+H)^+$.

(c) 5,6-Di-p-tolyl-pyrazine-2-carboxylic acid

The title compound was prepared as described in Preparation A step (a) using 4,4'-dimethylbenzil (848 mg, 3.56 mmol). The reaction mixture was however refluxed for 1 hour and air was bubbled through the reaction mixture for about 7 hours. The mixture was evaporated and the residue was dissolved in water. Hydrochloric acid (aq, 2 M) was added until pH 2 was reached. The solution was extracted with diethyl ether. The combined diethyl ether phases were dried ($MgSO_4$), filtered and evaporated under reduced pressure. The crude product (918 mg, 85%) was used in steps described below without further purification. MS m/z 305 $(M+H)^+$.

(d) 5,6-Bis-(4-methoxyphenyl)pyrazine-2-carboxylic acid

The title compound was prepared as described in Preparation A step (c) using 4,4'-dimethoxybenzil (961 mg, 3,56 mmol) as starting material. The reaction mixture was refluxed over night and air was bubbled through the mixture for 8 hours. The crude product (435 mg, 36%) was used in steps described below without further purification. MS m/z 335 (M+H)+

(e) 5,6-Bis-(4-chlorophenyl) pyrazine-2-carboxylic acid

The title compound was prepared as described in Preparation A step (c) using 4,4'-dichlorobenzil (993 mg, 3.56 mmol). Reflux for 1 hour gave directly the crude product (923 mg, 75%) that was used in steps described below without further purification. MS m/z 343, 345, 347 (M−H)⁻.

(f) 5,6-Bis-(2-chlorophenyl)pyrazine-2-carboxylic acid

The title compound was prepared as described in Preparation A step (c) using 2,2'-dichlorobenzil (993 mg, 3.56 mmol). The crude product (895 mg, 73%) was used in steps described below without further purification. MS m/z 343, 345, 347 (M−H)⁻.

(h) 1-(4-Chlorophenyl)-2-(2,4-dichlorophenyl) ethane-1,2-dione 2-(4-Chlorophenyl)-1-(2,4-dichlorophenyl)ethanone (2.7 g, 9.01 mmol) was dissolved in 1,2-dichloroethane (25 ml) and freshly made PCC (3.89 g, 18.02 mmol), pyridine (1.43 g, 18.02 mmol) and molecular sieves were added. The reaction mixture was refluxed under inert atmosphere overnight. The solution was cooled to 25° C., filtered through Silica and then solvent was evaporated under reduced pressure. The crude product (1.9 g, 66%) was used directly in the next step. $^1$H NMR (500 MHz) δ 7.97 (d, 2H), 7.84 (d, 1H), 7.52 (d, 2H), 7.46 (s, 1H), 7.44 (d, 1H).

(i) 5-(4-Chlorophenyl)-6-(2,4-dichlorophenyl)pyrazine-2-carboxylic acid and 6-(4-chlorophenyl)-5-(2,4-dichlorophenyl)pyrazine-2-carboxylic acid The title compounds were prepared as described in Preparation A step (a), using 1-(4-chlorophenyl)-2-(2,4-dichlorophenyl)ethane-1,2-dione (1.85 g; 5.90 mmol) from Preparation A step (g) and the monochloride of 2,3-diaminopropionic acid (0.61 g, 5.90 mmol) as starting materials. The mixture was refluxed for 30 minutes and then directly worked-up. The crude product was allowed to stand over night to aromatise. Flash chromatography (SiO₂, DCM: methanol 10:1, 1% Acetic acid) gave the isomer mixture (0.2 g, 10%). MS m/z 377, 379, 381 (M−H)⁻.

EXAMPLE 1

N-(1-piperidinyl)-5,6-diphenyl-2-pyrazinecarboxamide 5,6-Diphenyl-pyrazine-2-carboxylic acid (500 mg, 1.81 mmol) from Preparation A, step (a), was dissolved in DCM (4 ml) and DMF (150 µl). DMAP (22 mg, 0.18 mmol) and 1-aminopiperidine (218 mg, 2.17 mmol) were added and the solution was cooled to 0° C. A slurry of EDC (1.99 mmol, in 2 mL DCM and 100 µl DMF) was added dropwise. The reaction mixture was stirred at 25° C. After 17 hours additional 1-aminopiperidine (40 mg, 0.40 mmol) and EDC (76 mg, 0.40 mmol) was added, and the mixture was stirred for an additional 3 hours. The crude was diluted with DCM (5 ml) and washed with a saturated solution of NaHCO₃. The organic phase was dried (MgSO₄), filtered and evaporated. Flash chromatography (SiO₂, ethyl acetate:hexane 2:1) gave the subtitle compound (160 mg, 25%) as a white solid.

$^1$H NMR (300 MHz) δ 9.41 (s, 1H), 8.52 (s, 1H), 7.50-7.29 (m, 10H), 2.94 (t, 4H), 1.81 (m, 4H), 1.50 (m, 2H).

MS m/z 359 (M+H)⁺.

EXAMPLE 2

N-(1-piperidinyl)-5,6-bis(4-bromophenyl)-2-pyrazinecarboxamide

To 5,6-Bis-(4-bromophenyl)-pyrazine-2-carboxylic acid (108 mg, 0.25 mmol) from Preparation A, step (b), DMAP (0.025 mmol, in 500 µl DCM), 1-aminopiperidine (0.25 mmol, in 1100 µl DCM), EDC (0.27 mmol, in 1100 µl DCM and cooled to 8° C.) were added. The reaction mixture was stirred at 25° C. for 20 h, then washed with saturated NaHCO₃ solution, dried (MgSO₄), filtered and evaporated. Semipreparatory HPLC (0.01% TEA in the buffered phase) gave the subtitle compound (6.7 mg, 5.4%).

$^1$H NMR (300 MHz) δ 9.41 (s, 1H), 8.48 (s, 1H), 7.54 (d, 2H), 7.51 (d, 2H), 7.36 (d, 2H), 7.34 (d, 2H), 2.94 (t, 4H), 1.81 (m, 4H), 1.55-1.45 (m, 2H).

MS m/z 515, 517, 519 (M+H)⁺.

EXAMPLE 3

N-(1-piperidinyl)-5,6-bis(4-methylphenyl)-2-pyrazinecarboxamide 5,6-Di-p-tolyl-pyrazine-2-carboxylic acid (76 mg, 0.25 mmol) from Preparation A, step (c), was used as described in Example 2 to give the title compound (27 mg, 28%).

$^1$H NMR (300 MHz) δ 9.35 (s, 1H), 8.57 (s, 1H), 7.38 (d, 4H), 7.18 (d, 2H), 7.13 (d, 2H), 2.92 (t, 4H), 2.40 (s, 3H), 2.37 (s, 3H), 1.86-1.75 (m, 4H), 1.54-1.44 (m, 2H).

MS m/z 387 (M+H)⁺.

EXAMPLE 4

N-(1-piperidinyl)-5,6-bis(4-methoxyphenyl)-2-pyrazinecarboxamide 5,6-Bis-(4-methoxyphenyl)-pyrazine-2-carboxylic acid (84 mg, 0.25 mmol) from Preparation A, step (d), was used as described Example 2 to give the title compound (20 mg, 19%).

$^1$H NMR (300 MHz) δ 9.31 (s, 1H), 8.57 (s, 1H), 7.46 (d, 2H), 7.44 (d, 2H), 6.90 (d, 2H), 6.86 (d, 2H), 3.86 (s, 3H), 3.84 (s, 3H), 2.93 (t, 4H), 1.80 (m, 4H), 1.54-1.45 (m, 2H).

MS m/z 419 (M+H)⁺.

EXAMPLE 5

N-(1-piperidinyl)-5,6-bis(4-chlorophenyl)-2-pyrazinecarboxamide 5,6-Bis-(4-chlorophenyl)-pyrazine-2-carboxylic acid (86 mg, 0.25 mmol) from Preparation A, step (e), was used as described in Example 2 to give the subtitle compound (16 mg, 15%).

$^1$H NMR (300 MHz) δ 9.40 (s, 1H), 8.49 (s, 1H), 7.45-7.31 (m, 8H), 2.94 (t, 4H), 1.80 (m, 4H), 1.54-1.45 (m, 2H).

MS m/z 427, 429, 431 (M+H)⁺.

EXAMPLE 6

N-(1-piperidinyl)-5,6-bis(2-chlorophenyl)-2-pyrazinecarboxamide 5,6-Bis-(2-chlorophenyl)-pyrazine-2-carboxylic acid (86 mg, 0.25 mmol) from Preparation A, step (f), was used as described in Example 2 to give the subtitle compound (6 mg, 6%).

$^1$H NMR (300 MHz) δ 9.52 (s, 1H), 8.52 (s, 1H), 7.44-7.17 (d, 8H), 2.94-2.88 (t, 4H), 1.85-1.70 (m, 4H), 1.52-1.44 (m, 2H).

MS m/z 427, 429, 431 (M+H)$^+$.

EXAMPLE 7

N-cyclohexyl-5,6-diphenyl-2-pyrazinecarboxamide 5,6-diphenyl-pyrazine-2-carboxylic acid (70 mg, 0.25 mmol) from Preparation A, step (a), was reacted essentially as described in Example 2 but with cyclohexylamine (0.25 mmol, in 1 ml DCM), DMAP (0.025 mmol, in 0.5 ml DCM), EDC (0.28 mmol, in 1 ml DCM, and cooled to 8° C.) and DMF (100 µl). Semipreparatory HPLC (0.15% TFA/water:acetonitrile 95:5 instead of the buffer phase) gave the title compound (7 mg, 8%) after washing with Na$_2$CO$_3$ solution.

$^1$H NMR (300 MHz) δ 9.41 (s, 1H), 7.78 (d, 1H), 7.49-7.28 (m, 10H), 4.12-3.97 (m, 1H), 2.13-1.23 (m, 10H).

MS m/z 358 (M+H)$^+$.

EXAMPLE 8

N-cyclohexyl-5,6-bis(4-bromophenyl)-2-pyrazinecarboxamide 5,6-Bis-(4-bromophenyl)-pyrazine-2-carboxylic acid (109 mg, 0.25 mmol) from Preparation A, step (b), was used as described in Example 7. Semipreparatory HPLC (0.15% TFA/water:acetonitrile 95:5 instead of the buffer phase) gave the title compound (7 mg, 8%) after washing with Na$_2$CO$_3$ solution.

$^1$H NMR (300 MHz) δ 9.41 (s, 1H), 7.68 (s, 1H), 7.54 (d, 2H), 7.50 (d, 2H), 7.36 (d, 2H), 7.34 (d, 2H), 4.11-3.96(m, 1H), 2.12-1.20 (m, 10H).

MS m/z 514, 516, 518 (M+H)$^+$.

EXAMPLE 9

N-cyclohexyl-5,6-bis(4-methylphenyl)-2-pyrazinecarboxamide 5,6-Di-p-tolyl-pyrazine-2-carboxylic acid (76 mg, 0.25 mmol) from Preparation A, step (c), was used as described in Example 7. Semipreparatory HPLC (0.01% TEA in the buffer phase) gave the subtitle compound (4 mg, 4%).

$^1$H NMR (300 MHz) δ 9.36 (s, 1H), 7.77 (d, 1H), 7.39 (d, 4H), 7.18 (d, 2H), 7.13 (d, 2H), 4.10-3.96 (m, 1H), 2.40 (s, 3H), 2.37 (s, 3H), 2.09-1.20 (m, 10H).

MS m/z 386 (M+H)$^+$.

EXAMPLE 10

N-cyclohexyl-5,6-bis(4-methoxyphenyl)-2-pyrazinecarboxamide 5,6-Bis-(4-methoxyphenyl)-pyrazine-2-carboxylic acid (76 mg, 0.25 mmol) from Preparation A, step (d), was used essentially as described in Example 7 but the reaction mixture was first stirred overnight, then more cyclohexylamine (25 mg, 0.25 mmol) was added and the mixture was stirred for an additional two days prior to workup. Semipreparatory HPLC (0.15% TFA in the buffered phase) gave the title compound (12 mg, 11%).

$^1$H NMR (300 MHz) δ 9.32 (s, 1H), 7.76 (d, 1H), 7.47 (d, 2H), 7.45 (d, 2H), 6.90 (d, 2H), 6.86 (d, 2H), 4.10-3.96 (m, 1H), 3.86 (s, 3H), 3.84 (s, 3H), 2.09-1.17 (m, 10H).

MS m/z 418 (M+H)$^+$.

EXAMPLE 11

N-cyclohexyl-5,6-bis(4-chlorophenyl)-2-pyrazinecarboxamide 5,6-Bis-(4-chlorophenyl)pyrazine-2-carboxylic acid (86 mg, 0.25 mmol) from Preparation A, step (e), was used as described in Example 10 to give the title compound (7 mg, 8%) after washing with Na$_2$CO$_3$ solution.

$^1$H NMR (300 MHz) δ 9.41 (s, 1H), 7.69 (s, 1H), 7.47-7.30 (m, 8H), 4.10-3.97 (m, 1H), 2.10-1.18 (m, 10H).

MS m/z 426, 428, 430 (M+H)$^+$.

EXAMPLE 12

N-cyclohexyl-5,6-bis(2-chlorophenyl)-2-pyrazinecarboxamide 5,6-Bis-(2-chlorophenyl)-pyrazine-2-carboxylic acid (86 mg, 0.25 mmol) from preparation A step (f) was used as described in Example 10, to give the title compound (14 mg, 13%).

$^1$H NMR (300 MHz) δ 9.51 (s, 1H), 7.74 (s, 1H), 7.41-7.18 (m, 8H), 4.10-3.97 (m, 1H), 2.07-1.14 (m, 10H).

MS m/z 426, 428, 430 (M+H)$^+$.

EXAMPLE 13

N,5,6-triphenyl-2-pyrazinecarboxamide

To 5,6-Diphenyl-pyrazine-2-carboxylic acid (70 mg, 0.25 mmol) from Preparation A, step (a), DMAP (0.025 mmol, in 0.5 ml DCM), aniline (0.25 mmol, in 1 ml DCM), EDC (0.28 mmol, in 1 ml DCM, cooled to 8° C.) and DMF (100 µl) were added. The reaction mixture was stirred at 25° C. over night, then worked up as described in Example 2. Semipreparatory HPLC (0.15% TFA/water:acetonitrile 95:5 instead of the buffer phase) gave the title compound (27 mg, 30%) after washing with Na$_2$CO$_3$ solution.

$^1$H NMR (300 MHz) δ 9.75 (s, 1H), 9.52 (d, 1H), 7.80 (d, 2H), 7.55-7.32 (m, 12H), 7.20 (t, 1H).

MS m/z 352 (M+H)$^+$.

EXAMPLE 14

N-phenyl-5,6-bis(4-methylphenyl)-2-pyrazinecarboxamide 5,6-Di-p-tolyl-pyrazine-2-carboxylic acid (77 mg, 0.25 mmol) from Preparation A, step (c), was used as described in Example 13 to give the subtitle compound (28 mg, 29%).

$^1$H NMR (500 MHz) δ 9.78 (s, 1H), 9.49 (s, 1H), 7.81 (d, 2H), 7.47-7.43 (m, 6H), 7.25-7.17 (m, 5H), 2.45 (s, 3H), 2.41 (s, 3H).

MS m/z 380 (M+H)$^+$.

EXAMPLE 15

N-phenyl-5,6-bis(4-methoxyphenyl)-2-pyrazinecarboxamide 5,6-Bis-(4-methoxyphenyl)-pyrazine-2-carboxylic acid (85 mg, 0.25 mmol) from Preparation A step (d), was used as described in Example 13, to give the title compound (33 mg, 32%).

$^1$H NMR (300 MHz) δ 9.74 (s, 1H), 9.42 (s, 1H), 7.79 (d, 2H), 7.50 (d, 4H), 7.42 (t, 2H), 7.19 (t, 1H), 6.94 (d, 2H), 6.89 (d, 2H), 3.88 (s, 3H), 3.85 (s, 3H).

MS m/z 412 (M+H)$^+$.

EXAMPLE 16

N-phenyl-5,6-bis(4-chlorophenyl)-2-pyrazinecarboxamide 5,6-Bis-(4-chlorophenyl)-pyrazine-2-carboxylic acid (87 mg, 0.25 mmol) from Preparation A, step (e), was used as described in Example 13, to give the subtitle compound (6 mg, 6%).

$^1$H NMR (300 MHz) δ 9.66 (s, 1H), 9.52 (s, 1H), 7.79 (d, 2H), 7.48-7.35 (m, 10H), 7.21 (t, 1H).

MS m/z 420, 422, 424 (+H)$^+$.

EXAMPLE 17

N-phenyl-5,6-bis(2-chlorophenyl)-2-pyrazinecarboxamide 5,6-Bis-(2-chloro-phenyl)-pyrazine-2-carboxylic acid (87 mg, 0.25 mmol) from Preparation A, step (f), was treated as described in Example 13, to give the title compound (27 mg, 25%).

$^1$H NMR (500 MHz) δ 9.73 (s, 1H), 9.66 (s, 1H), 7.81 (d, 2H), 7.46-7.22 (m, 11H).

MS m/z 420, 422, 424 (M+H)$^+$.

EXAMPLE 18

5-(4-Chlorophenyl)-6-(2,4-dichlorophenyl)pyrazine-2-carboxylic acid piperidin-1-ylamide and 6-(4-chlorophenyl)-5-(2,4-dichlorophenyl)pyrazine-2-carboxylic acid piperidin-1-ylamide The mixture of 5-(4-chlorophenyl)-6-(2,4-dichlorophenyl)pyrazine-2-carboxylic acid and 6-(4-chlorophenyl)-5-(2,4-dichlorophenyl)pyrazine-2-carboxylic acid (78 mg, 0.205 mmol) from Preparation A step (i) and thionyl chloride (147 mg, 1.23 mmol) were refluxed in toluene (2 ml) for 3 hours. The solvent and reagents were evaporated under reduced pressure and the intermediates were dissolved in DCM (1 ml). TEA (42 mg, 0.41 mmol) and 1-aminopiperidine (21 mg, 0.205 mmol) were dissolved in DCM (1 ml) and added. The reaction mixture was stirred at 25° C. overnight and then evaporated under reduced pressure. Flash chromatography (SiO$_2$, heptane:ethyl acetate 1:1) gave a mixture of the title compounds (45 mg, 47%, ratio of isomers 0.5:1). $^1$H NMR (300 MHz) δ 9.46 (s, 1H), 8.39 (s, 1H), 7.47-7.28 (m, 7H), 3.02-2.84 (m, 4H), 1.89-1.73 (m, 4H), 1.57-1.41 (m, 2H) and 9.42 (s, 1H), 8.51 (s, 1H), 7.47-7.28 (m, 7H), 3.02-2.84 (m, 4H), 1.89-1.73 (m, 4H), 1.57-1.41 (m, 2H).

EXAMPLE 18 (A)

N-(1-piperidinyl)-5-(4-chlorophenyl)-6-(2,4-dichlorophenyl)-2-pyrazinecarboxamide The title compound was isolated from the mixture prepared in Example 18 (35 mg) by preparative chromatography (9 mg, 26%). $^1$H NMR (300 MHz) δ 9.46 (s, 1H), 8.38 (s, 1H), 7.46-7.24 (m, 7H), 2.89 (t, 4H), 1.78 (p, 4H), 1.52-1.40 (m, 2H).

EXAMPLE 18 (B)

N-(1-piperidinyl)-6-(4-chlorophenyl)-5-(2,4-dichlorophenyl)-2-pyrazinecarboxamide The title compound was isolated from the mixture prepared in Example 18 (35 mg) by preparative chromatography (11 mg, 31%). $^1$H NMR (300 MHz) δ 9.42 (s, 1H), 8.50 (s, 1H), 7.39-7.30 (m, 7H), 2.93 (t, 4H), 1.80 (p, 4H), 1.54-1.43 (m, 2H).

Pharmacological Activity

Compounds of Formula I are active against the receptor product of the CB1 gene. The affinity of the compounds of the invention for central cannabinoid receptors is demonstrable in methods described in Devane et al, Molecular Pharmacology, 1988, 34,605 or those described in WO01/70700 or EP 656354. Alternatively the assay may be performed as follows.

10 μg of membranes prepared from cells stably transfected with the CB1 gene were suspended in 200 μl of 100 mM NaCl, 5 mM MgCl$_2$, 1 mM EDTA, 5, mM HEPES (pH 7.4), 1 mM DTT, 0.1% BSA and 100 μM GDP. To this was added an EC80 concentration of agonist (CP55940), the required concentration of test compound and 0.1 μCi [$^{35}$S]-GTPγS. The reaction was allowed to proceed at 30° C. for 45 min. Samples were then transferred on to GF/B filters using a cell harvester and washed with wash buffer (50 mM Tris (pH 7.4), 5 mM MgCl$_2$, 50 mM NaCl). Filters were then covered with scintilant and counted for the amount of [$^{35}$S]-GTPγS retained by the filter.

Activity is measured in the absence of all ligands (minimum activity) or in the presence of an EC80 concentration of CP55940 (maximum activity). These activities are set as 0% and 100% activity respectively. At various concentrations of novel ligand, activity is calculated as a percentage of the maximum activity and plotted. The data are fitted using the equation y=A+((B−A)/1+((C/x)UD)) and the IC50 value determined as the concentration required to give half maximal inhibition of GTPγS binding under the conditions used.

The compounds of Formula I are active at the CB1 receptor (IC50<1 micromolar). Most preferred compounds have IC50<200 nanomolar.

The invention claimed is:

1. A process for the preparation of a stable dispersion of solid particles in an aqueous medium comprising:

combining (a) a first solution comprising a substantially water-insoluble substance which is a compound of Formula I

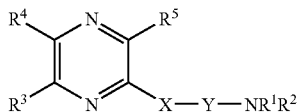

or a pharmaceutically acceptable salt thereof, in which
$R^1$ and $R^2$ independently are selected from a $C_{1-6}$alkyl group; an (amino)$C_{1-4}$alkyl- group in which the amino is optionally substituted by one or more $C_{1-3}$alkyl groups; an optionally substituted non-aromatic $C_{3-15}$carbocyclic group; a $(C_{3-12}$cycloalkyl)$C_{1-3}$alkyl- group; a group—$(CH_2)_r$(phenyl)$_s$ in which r is 0, 1, 2, 3 or 4, s is 1 when r is 0 otherwise s is 1 or 2 and the phenyl groups are optionally independently substituted by one, two or three groups represented by Z; naphthyl; anthracenyl; a saturated 5 to 8 membered heterocyclic group containing one nitrogen and optionally one of the following: oxygen, sulphur or an additional nitrogen wherein the heterocyclic group is optionally substituted by one or more $C_{1-3}$alkyl groups, hydroxy or benzyl; 1-adamantylmethyl; and a group —$(CH_2)_t$Het in which t is 0, 1, 2, 3 or 4, and the —$(CH_2)_t$ moiety is optionally substituted by one or more $C_{1-3}$alkyl groups and Het represents an aromatic heterocycle optionally substituted by one, two or three groups selected from a $C_{1-5}$alkyl group, a $C_{1-5}$alkoxy group and halo;

or $R^1$ represents H and $R^2$ is as defined above;

or $R^1$ and $R^2$ together with the nitrogen atom to which they are attached represent a saturated 5 to 8 membered heterocyclic group containing one nitrogen and optionally one of the following: oxygen, sulphur or an additional nitrogen; wherein the heterocyclic group is optionally substituted by one or more $C_{1-3}$alkyl groups, hydroxy or benzyl;

X is CO or $SO_2$;

Y is absent or is NH optionally substitututed by a $C_{1-3}$alkyl group;

$R^3$ and $R^4$ independently are selected from phenyl, thienyl and pyridyl, each of which is optionally substituted by one, two or three groups represented by Z;

Z represents a $C_{1-3}$alkyl group, a $C_{1-3}$alkoxy group, hydroxy, halo, trifluoromethyl, trifluoromethylthio, trifluoromethoxy, trifluoromethylsulphonyl, nitro, amino, mono or di $C_{1-3}$alkylamino, mono or di $C_{1-3}$alkylamido, $C_{1-3}$alkylsulphonyl, $C_{1-3}$alkoxycarbonyl, carboxy, cyano, carbamoyl, mono or di $C_{1-3}$alkyl carbamoyl, sulphamoyl or acetyl; and $R^5$ is H, a $C_{1-3}$alkyl group, a $C_{1-3}$alkoxymethyl group, trifluoromethyl, a hydroxy$C_{1-3}$alkyl group, $C_{1-3}$alkoxycarbonyl, carboxy, cyano, carbamoyl, mono or di $C_{1-3}$alkylcarbamoyl, acetyl, or hydrazinocarbonyl of formula —$CONHNR^aR^b$ wherein $R^a$ and $R^b$ are as previously defined for $R^1$ and $R^2$ respectively;

a water-miscible organic solvent and an inhibitor with (b) an aqueous phase comprising water and optionally a stabiliser, thereby precipitating solid particles comprising the inhibitor and the substantially water-insoluble substance; and optionally removing the water-miscible organic solvent;

wherein:
the inhibitor is less soluble in water than the water-insoluble substance, and the inhibitor is selected from one or more of:

(i) a mono-, di- or a tri-glyceride of a fatty acid;
(ii) a fatty acid mono- or di-ester of a $C_{2-10}$ diol;
(iii) a fatty acid ester of an alkanol or a cycloalkanol;
(iv) a wax;
(v) a long chain aliphatic alcohol of 6 to 30 carbon atoms; and
(vi) a hydrogenated vegetable oil.

2. A process according to claim 1, wherein the inhibitor is a mixture of triglycerides obtainable by esterifying glycerol with a mixture of medium chain fatty acids.

3. A process according to claim 2, wherein the inhibitor is a mixture of triglycerides containing acyl groups with from 8 to 12 carbon atoms.

4. A process according to claim 1, wherein the inhibitor further comprises a co-inhibitor selected from a long chain aliphatic alcohol containing 6 30 carbon atoms.

5. A process according to claim 1, wherein the inhibitor is sufficiently miscible with the substantially water-insoluble substance to form solid particles in the dispersion comprising a substantially single phase mixture of the substance and the inhibitor.

6. A process according to claim 1, wherein the miscibility of the inhibitor and substantially water-insoluble substance is sufficient to give an interaction parameter χ of less than 2.5.

7. A process according to claim 1, wherein the aqueous phase contains a stabiliser.

8. A process according to claim 7, wherein the stabiliser comprises a polymeric dispersant and a surfactant.

9. A process according to claim 1, wherein the mean particle size of the solid particles is less than 1 μm.

10. A process according to claim 1, farther comprising isolating the solid particles from the dispersion.

11. A process for the preparation of a stable dispersion of solid particles in an aqueous medium comprising combining (a) a first solution comprising a substantially water-insoluble substance, a water-miscible organic solvent, and an inhibitor with (b) an aqueous phase comprising water and optionally, a stabilizer, thereby precipitating solid particles comprising the inhibitor and the substantially water-insoluble substance; and optionally removing the water-miscible organic solvent;

wherein:
the inhibitor is less soluble in water than the water-insoluble substance, and the inhibitor is selected from one or more of:
a mono-, di- or a tri-glyceride of a fatty acid;
(ii) a fatty acid mono- or di-ester of a $C_{2-10}$ diol;
(iii) a fatty acid ester of an alkanol or a cycloalkanol;
(iv) a wax;
(v) a long chain aliphatic alcohol of 6 to 30 carbon atoms; and
(vi) a hydrogenated vegetable oil; and wherein the substantially water-insoluble substance is selected from:
N-(1-piperidinyl)-5,6-diphenyl-2-pyrazinecarboxamide;
N-(1-piperidinyl)-5,6-bis(4-bromophenyl)-2pyrazinecarboxamide;
N-(1-piperidinyl)-5,6-bis(4-bromophenyl)-2pyrazinecarboxamide;
N-(1-piperidinyl)-5,6-bis(4-methoxyphenyl)-2-pyrazinecarboxamide;
N-(1-piperidinyl)-5,6-bis(4-chlorophenyl)-2-pyrazinecarboxamide;
N-(1-piperidinyl)-5,6-bis(4-chlorophenyl)-2-pyrazinecarboxamide;
N-cyclohexyl-5,6-diphenyl-2-pyrazinecarboxamide;
N-cyclohexyl-5,6-bis(4-bromophenyl)-2-pyrazinecarboxamide;

N-cyclohexyl-5,6-bis(4-methylphenyl)-2-pyrazinecarboxamide;
N-cyclohexyl-5,6-bis(4-methoxyphenyl)-2-pyrazinecarboxamide;
N-cyclohexyl-5,6-bis(4-chlorophenyl)-2-pyrazinecarboxamide;
N-cyclohexyl-5,6-bis(2-chlorophenyl)-2-pyrazinecarboxamide;
N,5,6-triphenyl-2-pyrazinecarboxamide;
N-phenyl-5,6-bis(4-methylphenyl)-2-pyrazinecarboxamide;
N-phenyl-5,6-bis(4-methoxyphenyl)-2-pyrazinecarboxamide;
N-phenyl-5,6-bis(4-chlorophenyl)-2-pyrazinecarboxamide;
N-phenyl-5,6-bis(2-chlorophenyl)-2-pyrazinecarboxamide;
N-(1-piperidinyl)-5-(4-chlorophenyl)-6-(2,4-dichlorophenyl)-2-pyrazinecarboxamide; and
N-(1-piperidinyl)-6-(4-chlorophenyl)-5-(2,4-dichlorophenyl)-2-pyrazinecarboxamide;

or, where applicable, an optical isomer, tautomer, stereoisomer, or racemate thereof, or a pharmaceutically acceptable salt thereof.

* * * * *